(12) United States Patent
Orlowski

(10) Patent No.: US 6,852,117 B2
(45) Date of Patent: Feb. 8, 2005

(54) MEDICAL KNIFE ASSEMBLY AND METHOD OF USING SAME

(75) Inventor: Boguslaw Orlowski, Oceanside, CA (US)

(73) Assignee: Medical Device Group, Inc., Poway, CA (US)

( * ) Notice: Subject to any disclaimer, the term of this patent is extended or adjusted under 35 U.S.C. 154(b) by 104 days.

(21) Appl. No.: 10/224,895

(22) Filed: Aug. 21, 2002

(65) Prior Publication Data

US 2003/0004521 A1 Jan. 2, 2003

Related U.S. Application Data

(63) Continuation-in-part of application No. 09/614,242, filed on Jul. 12, 2000, now abandoned.

(51) Int. Cl.[7] ............................................. A61B 17/42
(52) U.S. Cl. ...................................... 606/120; 606/157
(58) Field of Search .................................. 606/120, 157, 606/151, 207, 205, 208

(56) References Cited

U.S. PATENT DOCUMENTS

| | | | |
|---|---|---|---|
| 3,631,858 A | | 1/1972 | Ersek |
| 4,716,886 A | * | 1/1988 | Schulman et al. ............ 606/120 |
| 4,938,215 A | * | 7/1990 | Schulman et al. ............ 606/120 |
| 5,046,252 A | | 9/1991 | Ayuta et al. |
| 5,190,556 A | | 3/1993 | Hessel |
| 5,584,840 A | * | 12/1996 | Ramsey et al. ............... 606/120 |
| 5,667,516 A | | 9/1997 | Allen |
| 5,676,672 A | * | 10/1997 | Watson et al. ............... 606/120 |
| 5,913,862 A | * | 6/1999 | Ramsey et al. ............... 606/120 |
| 5,937,523 A | | 8/1999 | Van Keppel et al. |
| 5,947,980 A | * | 9/1999 | Jensen et al. ................ 606/120 |
| 5,968,054 A | * | 10/1999 | Yeatts et al. ................. 606/120 |
| 5,997,548 A | | 12/1999 | Jahanger |
| 6,348,057 B1 | * | 2/2002 | Porat ........................... 606/120 |
| 6,682,538 B2 | * | 1/2004 | Qiu et al. ..................... 606/120 |

* cited by examiner

*Primary Examiner*—Pedro Philogene
(74) *Attorney, Agent, or Firm*—Jerry R. Potts

(57) ABSTRACT

A medical knife assembly includes an outer clamp assembly and an inner clamp blade assembly having a cutting blade assembly. The inner and outer clamp assemblies are pivotally connected at about their proximate ends so they may be squeezed together with one hand to affect a novel method of clamping and cutting in a single motion operation. A set of shear pins holds the component parts of the inner and outer assemblies together in a ready position that enables a user to properly position the knife assembly for severing an umbilical cord at the time of birth. Once the umbilical cord is severed, the component parts of the inner and outer assemblies separate providing independent clamps, one staying with an infant segment of the umbilical cord and one staying with a maternal segment of the umbilical cord. The two independent clamps operate to clamp the umbilical cord on both sides of the cutting blade assembly thereby preventing or at least greatly

8 Claims, 3 Drawing Sheets

MEDICAL KNIFE ASSEMBLY AND METHOD OF USING SAME

CROSS REFERENCES TO RELATED APPLICATIONS

This is a continuation-in-part patent application of U.S. patent application Ser. No. 09/614,242 filed Jul. 12, 2000 now abandoned, entitled: "Blood Fee Medical Knife with Double Clamps".

FIELD OF INVENTION

This invention relates to a cutting and clamping mechanism, and more particularly to a cutting and clamping mechanism for use in obstetrics for severing and clamping an umbilical cord.

BACKGROUND OF INVENTION

Cutting assemblies are well known in the art. For example, reference may be made to the following U.S. patent documents: U.S. Pat. Nos. 3,631,858; 4,716,886; 4,938,215; 5,046,252; 5,190,556; 5,584,840; 5,667,516; 5,676,672; 5,913,862; 5,937,523; 5,968,054; and 5,997,548.

The severance of an umbilical cord occurs shortly after birth. The umbilical cord functions to provide a fetus with oxygen and nutrients during the gestation period. Once a child has been born, the umbilical cord needs to be severed. In the regard, an obstetrician, or other practitioner tends to this task by first clamping the cord to reduce blood flow and then severs the cord, thus freeing the fetus from the mother. At the moment before the umbilical cord is severed, it is engorged with blood under pressure from both the mother and the fetus and thus, when severed blood and amniotic fluid escape and flow onto the gloved hands of the obstetrician. Such fluids on the gloved hands of the obstetrician become very slippery and thereby increased risk of an accident, such as the possibility of the obstetrician dropping the infant as the infant is moved away from the mother. Moreover, with the increased risk of blood borne infections from viral agents such as HIV, hepatitis and other diseases such as AIDS, it would be highly desirable to have a new and improved cutting apparatus and method that eliminates or at least greatly reduces such risks.

SUMMARY OF THE INVENTION

A medical knife assembly includes an outer clamp assembly and an inner clamp blade assembly having a cutting blade assembly. The inner and outer clamp assemblies are pivotally connected at about their proximate ends so they may be squeezed together with one hand to affect a novel method of clamping and cutting in a single motion operation. A set of shear pins holds the component parts of the inner and outer assemblies together in a ready position that enables a user to properly position the knife assembly for severing an umbilical cord at the time of birth. Once the umbilical cord is severed, the component parts of the inner and outer assemblies separate providing independent clamps, one staying with an infant segment of the umbilical cord and one staying with a maternal segment of the umbilical cord. The two independent clamps operate to clamp the umbilical cord on both sides of the cutting blade assembly thereby preventing or at least greatly reducing the flow of blood from around the clamps at the time of severance.

BRIEF DESCRIPTION OF THE DRAWINGS

The above mentioned features and steps of the invention and the manner of attaining them will become apparent, and the invention itself will be best understood by reference to the following description of the embodiments of the invention in conjunction with the accompanying drawings wherein.

DESCRIPTION OF THE PREFERRED EMBODIMENT

Figure 1:
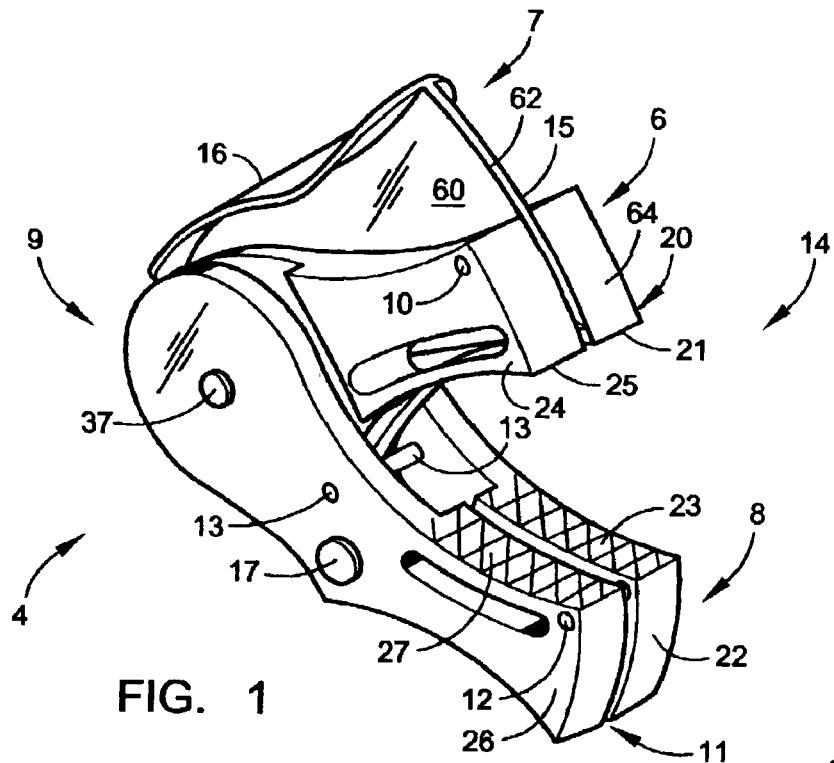
FIG. 1 is a perspective view of a knife assembly, which is constructed in accordance with the present invention.

Referring now to the drawings and more particularly to FIG. 1 thereof, there is illustrated a disposable medical knife assembly 4, which is constructed in accordance with the present invention. The knife assembly 4 is designed specifically for clamping and severing an umbilical cord with one simple motion with a consistent predetermined amount of hand pressure force of between about ten pounds of pressure and about twelve pounds of pressure which insures precise cutting as will be explained hereinafter in greater detail. The size of the disposable knife assembly 4 is specifically designed to fit any size of umbilical cord and to be easily held in one hand to affect a novel method of clamping and cutting in a single motion operation. More specifically this specification will describe a medical knife assembly 4 that is designed to sever the umbilical cord by clamping the umbilical cord on both the fetal and the maternal side and simultaneously cutting the cord. The knife assembly 4 as will be explained hereinafter in greater details has two independent clamps that are spaced apart from one another and that separate after severing the cord. In this regard one clamp remains on fetal side of the umbilical cord and one clamp remains on the maternal side of the umbilical cord there by trapping blood in each segment. This technique results in a reduced loss of blood during the cutting process. Moreover cord blood entrapped in both segments of the cord can be harvested for further diagnostic procedures. The knife assembly 4 also employs a plurality of shear pins that requires the user to apply a specific amount of force to server the cord thus creating a uniform cut. One of the clamps, and more specifically the maternal clamp has a quick release mechanism that enables the rapid harvesting of blood. The closely parallel dual clamps reduce the amount of blood entrapped at the point of severance of the cord that further reduces fluid loss and exposure. The knife assembly 4 is designed to be the correct size to enable the user to produce the cut using one hand.

Figure 2:
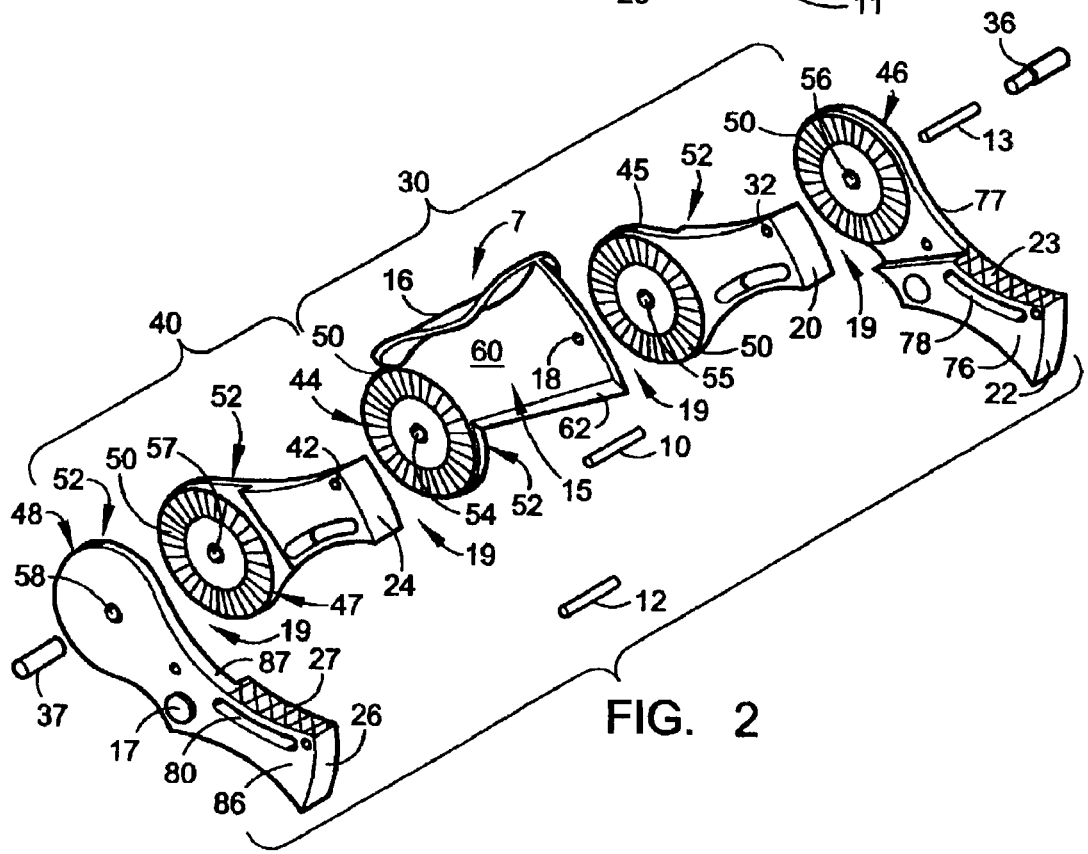
FIG. 2 is an exploded view of the knife assembly of FIG. 1.

Considering now the knife assembly 4 in greater detail with reference to FIGS. 1 and 2, the knife assembly 4 generally comprises an inner clamp blade assembly indicated generally at 6 and an outer clamp assembly indicated generally at 8. A pivot pin assembly 9 pivotally connects the inner clamp blade assembly 6 and the outer clamp assembly 8 so they may be squeezed together with one hand to affect the novel method of clamping and cutting in a single motion operation. A stop shear pin 13 disposed in the outer clamp assembly 8 holds the distal ends of the inner clamp blade assembly 6 and the outer clamp assembly 8 a sufficient distance apart to define an umbilical cord receiving space indicated generally at 14. The umbilical cord receiving space 14 is sufficiently large to receive any size umbilical cord. As will be explained hereinafter in greater detail, when the stop shear pin 13 is severed, the inner clamp blade assembly 6 and the outer clamp assembly 8 are free to pivot together in a locking configuration for umbilical cord clamping and simultaneous cutting purposes.

As best seen in FIGS. 1–2, the inner clamp blade assembly 6 includes a lockable slideable blade assembly 7 having a cutting blade 15 and a no-skid concave finger grip or saddle 16. The finger grip 16 enable a user of the knife assembly 4 to comfortably and easily grip the knife assembly 4 in one hand with the fingers of the user resting on the saddle 16 and the thumb of the user extending across the under surface of the outer clamping assembly 8. The finger grip 16 also functions as a stop to limit the travel of the blade assembly 7 as it slides from within the inner blade clamp assembly 6 and into a blade receiving space 11 that is disposed within the outer clamp assembly 8.

As will be explained hereinafter in greater detail a pair of shear pins that includes an inner shear pin 10 and an outer shear pin 12 not only help secure together the component parts of the inner assembly 6 and the outer assembly 8 respectively, but also function to insure a clean severance of the cord with a blade shearing force of between about ten pounds of pressure and about twelve pounds of pressure.

The inner assembly 6 includes a pair of inner clamping members and more specifically an inner neonatal clamping member 20 and an inner maternal clamping member 24. The inner clamping members 20 and 24 each has a generally plano-concave structure at about their respective distal end portions with serrated gripping surfaces indicated generally at 21 and 25 respectively. The serrated gripping surfaces 21 and 25 help grip and secure an umbilical cord as it is clamped between the inner assembly 6 and the outer assembly 8.

In a similar manner, the outer assembly 8 includes a pair of outer clamping members and more specifically an outer neonatal clamping member 22 and an outer maternal clamping member 26. The outer clamping members 22 and 26 are generally plano-concave in structure at about their respective distal end portions and have serrated gripping surfaces generally indicated at 23 and 27 respectively for cooperating with the gripping surfaces 21 and 25 of the inner clamping members 20 and 24 to insure that an umbilical cord clamped between the inner assembly 6 and the outer assembly 8 is tightly gripped for an immediate cutting operation.

Considering now the method of using the medical knife assembly 4 for clamping and severing an umbilical cord, a user (not shown) grasp the knife assembly 4 between the thumb and the remaining fingers of the hand of the user. In this regard, the fingers are disposed on the finger saddle 7 of the inner blade clamp assembly 6 with the thumb disposed on the under surface of the outer clamp assembly 8. The user next, moves the knife assembly 4 into contact with the umbilical cord so that the umbilical cord is received within the umbilical cord receiving space 14. With the umbilical cord disposed within the space 14, the user squeezes the knife assembly 4 with a sufficient amount of pressure to break the stop shear pin 13 thereby allowing the distal end portions of the inner assembly 6 and the outer assembly 8 to firmly clamp the umbilical cord. In this regard, as the user continues to squeeze the knife assembly 4, the relative pressure exerted on the inner assembly 6 and the outer assembly 8 causes the blade shear pin 10 to break under a pressure of between about ten pounds and about twelve pounds of pressure. Upon the breaking of the blade shear pin 10, the blade 15 slides out from the inner assembly 6 and into the blade receiving space 11 of the outer assembly 8 as the blade 15 passes through and severs the umbilical cord. The travel of the blade 15 is halted in a locked position when the undersurface of the finger saddle 16 comes into contact with the top portions of the inner clamping members 20 and 24 respectively. In this locked position, the blade assembly 7 remains attached to the inner clamping member 20 and the outer clamping member 22, which pair of inner and outer clamping members 20, 22 now define a neonatal clamp arrangement indicated generally at 30. The remaining components of the medical knife assembly 4, including the inner clamping member 24 and the outer clamping member 26 define a maternal clamp arrangement indicated generally at 40. It should be understood by those skilled in the art, that once the shear pins 10, 12 and 13 have been broken, the two independent clamp arrangements 30 and 40 are separated from one another allowing the infant segment of the umbilical cord to be moved toward the infant and the maternal segment of the umbilical cord to be moved toward the mother. In this regard, should the user desire to harvest a blood sample from the maternal clamp side of the umbilical cord, the user can depress a quick release button 17 forming part of the outer assembly 8 causing the pair of inner and outer clamp members on the maternal side of the blade 15 to separate and thus temporarily releasing the umbilical cord on the maternal side for rapid blood harvesting.

Considering now the disposable knife assembly 4 in greater detail with reference to FIGS. 1 and 2, the knife assembly 4 generally comprises the pair of independent clamp arrangements that includes the neonatal clamp arrangement indicated generally at 30 and the maternal clamp arrangement indicated generally at 40. The neonatal clamp arrangement 30 as noted before, includes the inner neonatal clamping member 20 and the outer neonatal clamping member 22. The pivot pin assembly 9, pivotally connects the inner neonatal clamping member 20 and the outer neonatal clamping member 22. In a similar manner, the maternal clamp arrangement 40 includes the inner maternal clamping member 24 and the outer maternal clamping member 26. The pivot pin assembly 9 also pivotally connects the inner maternal clamping member 24 and the outer maternal clamping member 26.

Considering now the pivot pin assembly 9 in greater detail with reference to FIG. 2, the pivot pin assembly 9 generally includes a pair of pin caps, which includes a right side pin cap 36, and a left side pin cap 37. The right side pin cap 36 and the left side pin cap 37 are each dimensioned to fit within a pivot pin aperture, such as the pivot pin aperture 58, that is disposed at about the proximate end portion each of the various components of the knife assembly 4 which includes the blade assembly 7, the inner neonatal clamping segment 20, the outer neonatal clamping segment 22, the inner maternal clamping segment 24 and the outer maternal clamping segment 26. As best seen in FIG. 2, the right side pin cap 36 is further dimensioned to hold in an assembled condition the neonatal clamping arrangement 30, which when separated from the maternal clamping arrangement 40, has the blade assembly 7 attached thereto. In a similar manner the cap pin 37 is dimensioned to hold in an assembled condition the maternal clamping arrangement 40. From the foregoing, it should be understood by those skilled in the art, that once the shear pins 10, 12, and 13 have been severed, the neonatal clamping arrangement 30 and the maternal clamping arrangement 40 can be easily separated from one another allowing the clamped segments of the infant side of the blade assembly 7 to be moved with the infant and the clamped segments of the maternal side of the blade assembly 7 to be moved with the mother. This is an important feature of the present invention.

As best seen in FIG. 1, the lockable blade 15 is sandwiched between the inner neonatal clamping member 20 and the inner maternal clamping member 24 and is held in place between them by the pivot pin assembly 9 and the blade shear pin 10. In this regard, the shear pin 10 passes through a blade aperture 18 disposed in the blade 15, locking the blade 15 in place between the inner neonatal clamping member 20 and the inner maternal clamping member 24. An inner neonatal clamping aperture 32 and an inner maternal clamping aperture 42 are dimensioned to receive in a friction tight fit, the shear pin 10. In this regard, the shear pin 10 is sufficiently long to extend through the inner neonatal clamping member 20, the blade 15 and the inner maternal clamping member 24 and cooperates with a pivot pin cap 36 forming part of the pivot pin assembly 9, to hold the blade 15 firmly between the inner neonatal clamping member 20 and the inner maternal clamping member 24. The blade 15 will be held securely between the inner members 20 and 24 until a sufficient amount of pressure force is applied to the blade assembly 7 to allow it to shear the shear pin 10 with a pressure force of between about 10 pounds of pressure and about 12 pounds of pressure.

In order to facilitate locking the blade assembly 7 between the inner neonatal clamping member 20 and the inner maternal clamping member 24, the blade assembly 7, as well as the clamping members 20,24 each include a locking arrangement indicated generally at 19. As each of the locking arrangements 19 are substantially similar only a single locking arrangement 19 will be described hereinafter in greater detail.

The locking arrangement 19 generally includes a pair of spaced apart circular splines, such as a spline 50 and 52. The spline 50 includes a series of uniformly spaced ridges and valleys that are dimensioned so that the ridges and valleys interlock with a like set of spaced apart ridges and valleys that are disposed on the opposing face portion of the spline 52. Due to the interlocking arrangement between the ridges and valleys of the splines 50 and 52, the components carrying the respective splines interlock and pivotally rotate together as the blade 15 is moved into the blade receiving space 11.

Considering now the blade shear pins 10 and 12 as well as the stop pin 13, each of the pins 10, 12, and 13 are composed of an inert plastic material that breaks under a shear force of between about ten pounds of pressure and about twelve pounds of pressure. The exertion of this force occurs when the blade assembly 7 is moved pivotally in unison with the inner assembly 6 a sufficient distance to break the stop shear pin 13 thereby allowing the inner assembly 6 and the outer assembly 8 to come together in a clamping like manner. As the inner assembly 6 and the outer assembly 8 come towards one another to clamp the umbilical cord disposed within the umbilical cord space 14, further pressure on the blade assembly 7 causes the blade shear pin 10 to snap allowing the blade 15 to pass through the umbilical cord. The blade 15 continues its travel into the blade receiving space 11 where the blade 15 breaks or shears the other blade shear pin 12. The motion of blade 15 is halted when the underside of the finger grip 16 engages the tops of the inner neonatal clamping member 20 and the inner maternal clamping member 24.

Figure 4:
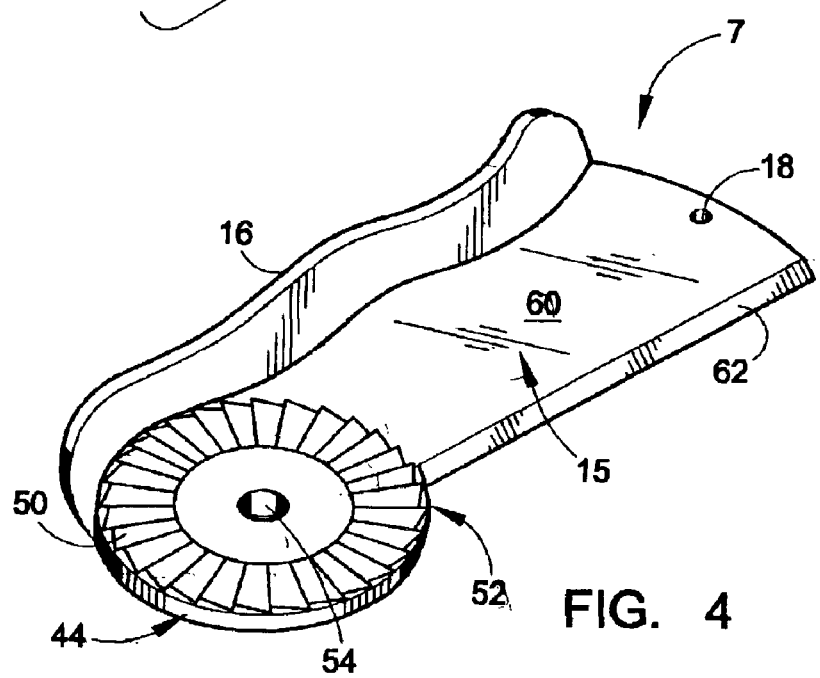
FIG. 4 is an enlarged perspective view of a blade assembly forming part of the knife assembly of FIG. 1.
Figure 6:
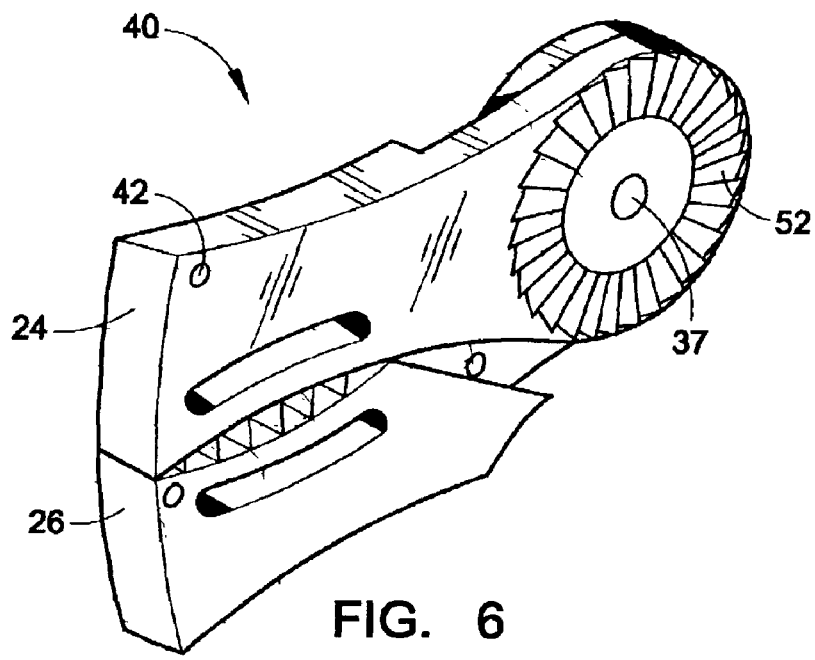
FIG. 6 is a perspective view of a maternal clamping arrangement resulting from the separation of the knife assembly of FIG. 1.
Figure 5:
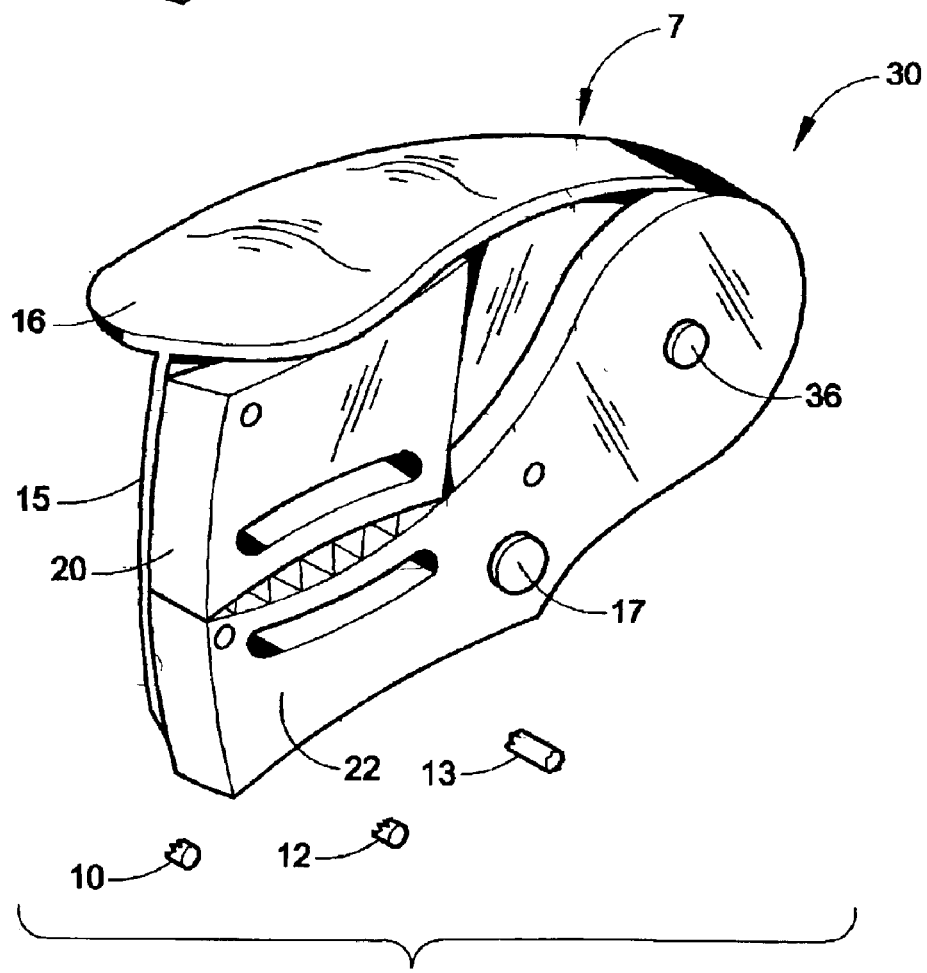
FIG. 5 is a perspective view of a neonatal clamping arrangement resulting from the separation of the knife assembly of FIG. 1.

Considering now the blade assembly 7 in greater detail with reference to FIG. 4, the blade assembly generally includes the blade 15, the finger grip 16, and a circular base member 44. On each face portion of the base member 44 there is disposed a spline, such as the spline 50 and the spline 52, the forms part of the locking arrangement 19 as noted before. A pivot pin aperture 54 is disposed at the geometric center of the base member 44. The splines 50 and 52 are spaced from the geometric center of the base member 44 in a radial arrangement that terminates at outer periphery of the base member 44. The blade 15 is integrally connected to an outer segment portion of the base member 44 and extends outwardly therefrom in a parallel plane forming a wall like structure 60. The base or bottom portion of the wall 60 is formed into a sharp triangularly shaped cutting edge 62 that extends the entire length of the wall 60 terminating at the outer periphery of the base member 44. In this regard, the length of the wall is chosen to be sufficient long to be able to cut any size umbilical cord in a clean precise manner. The wall 60 has a thickness dimension that enables the blade wall 60 to easily slide between the two inner clamping components 20 and 24 when assembled. As will be explained hereinafter, a front edge 62 of the wall is in a smooth plano-convex configuration that corresponds in its radial dimension to a front wall portion 64 of the inner clamping components 20 and 24 respectively. In this manner, the front walls of the inner clamping components as well as the front edge 62 of the blade wall 60 present smooth non cutting surfaces allowing the knife assembly 4 to be easily handled without the danger of cutting the user, mother or infant in an accidental manner.

In order for the blade assembly 7 to be properly aligned relative to the inner clamping components 20 and 24, the assembly 7 and each of the components 20 and 24 include blade shear alignment holes 18, 32, and 42 respectively Aligning the holes 18, 32, and 42 and then inserting the blade shear pin 10 through them therefore accomplish an assembly alignment. From the foregoing, it should be understood that the shear pin 10 has a secondary function, which is to hold the blade assembly 7 and the component parts 20 and 24 in an aligned assembled position. It should also be understood that the combined front wall dimensions of the assembly 7 and each of the components 20 and 24 is substantially the same as the over-all length of the blade shear pin 10, so that the pin 10 does not protrude beyond the outer wall dimensions of the components 20 and 24 when inserts through the holes 18, 32 and 42.

As best seen in FIGS. 1 and 4, the finger grip 16 is integrally attached to the top of wall 60 and is configured in an irregular oval configuration having a wave-like form This form allows the finger of the user to rest and grip against this platform without slipping. The upper surface of the finger grip 16 is also coated with a non-skid material, the help assure that the fingers of the user will not easily slip from this platform when in use.

Considering now the inner clamping components 20 and 24 in greater detail, only the inner component 20 will be described in greater detail, as both components 20 and 24 are substantially the same in configuration and dimension.

Figure 3:
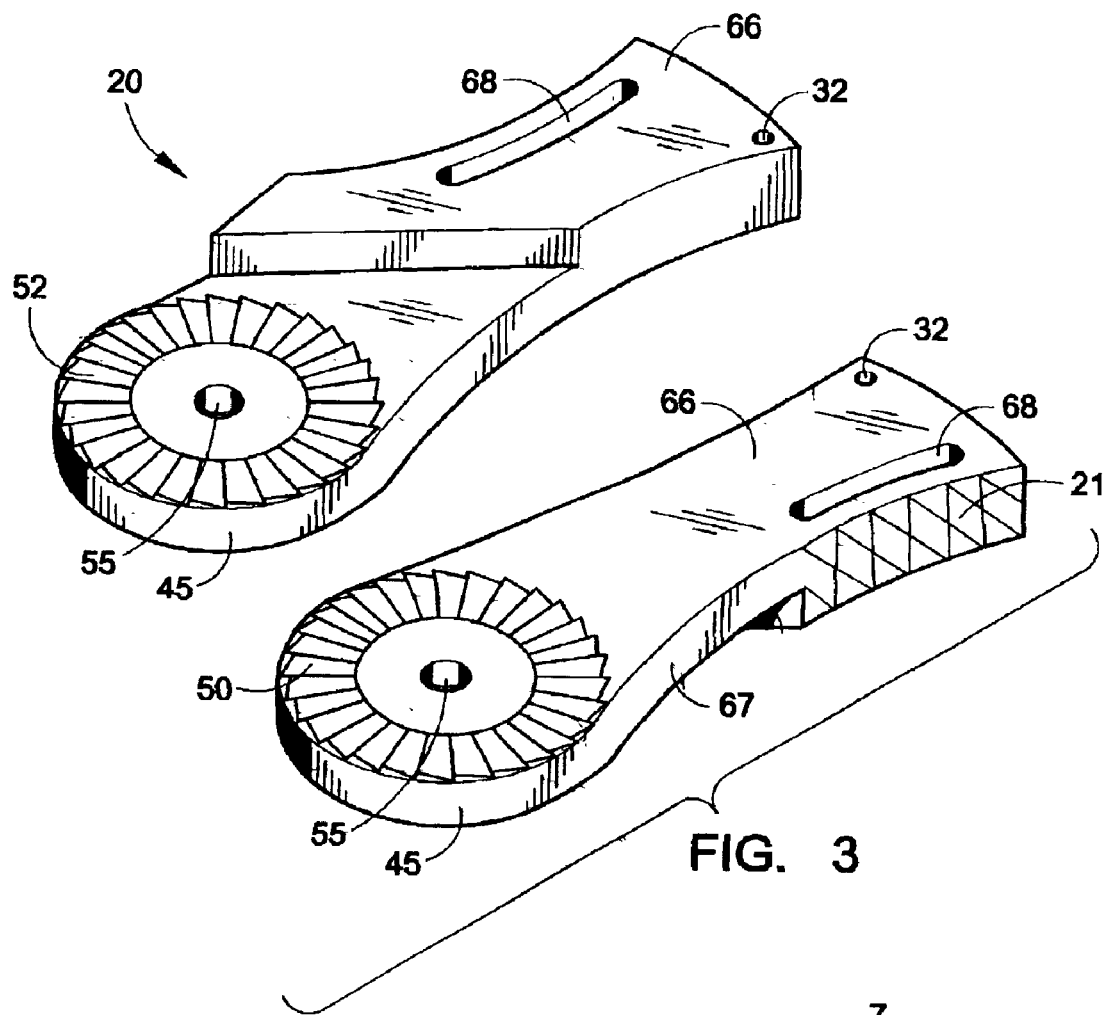
FIG. 3 is an enlarged perspective view of an inner clamping component of the knife assembly of FIG. 1, showing its right and left sides.

As best sen in FIG. 3, the inner clamping component 20 generally includes a circular base member 45 and wall 66 that is integrally connected to an outer segment portion of the base member 45. On each face portion of the base member 45 there is disposed a spline, such as the spline 50 and the spline 52, the forms part of the locking arrangement 19 as noted before. A pivot pin aperture 55 is disposed at the geometric center of the base member 45. The splines 50 and 52 are spaced from the geometric center of the base member 44 in a radial arrangement that terminates at outer periphery of the base member 45.

The wall 66 extends outwardly from the base member 45 in a parallel plane forming an anvil like structure. A base or bottom portion 67 of the wall 66 is in a piano-concave form with a distal end portion of the base 67 having a serrated surface 21 that facilitates the clamping of the umbilical cord. An elongated oval shaped window 68 is disposed in the wall 66 in order to allow any residual blood or umbilical cord tissue to escape from within the knife assembly 4 during the cutting operation. In this regard, the window 68 has a concave form that corresponds to the plano-concave form of the clamping surface wall 67.

The wall 66 has a thickness dimension that provides a sufficient clamping surface to handle any sized umbilical cord. The front edge 64 of the wall 66 is in a smooth plano-convex configuration that corresponds in its radial dimension to the front edge wall 62 of the blade wall 60 and the front wall of the inner clamping component 24 respectively. In this manner, the front walls of the inner clamping components as well as the front edge 62 of the blade wall 60 present smooth non cutting surfaces allowing the knife assembly 4 to be easily handled without the danger of cutting the user, mother or infant in an accidental manner.

In order for the clamping component 20 to be properly aligned relative to the inner clamping component 24 and the blade assembly 7 the wall 66 includes the blade shear alignment hole 32. Aligning the hole 32 with the other alignment holes 18 and 42 and then inserting the blade shear pin 10 through them therefore accomplish an alignment.

Considering the outer clamping component 22 in greater detail with reference to FIG. 2, the outer clamping component 22 generally includes a circular base member 46 and wall 76 that is integrally connected to an outer segment portion of the base member 46. On the inner face portion of the base member 46 there is disposed a spline, such as the spline 50, the forms part of the locking arrangement 19 as noted before. A pivot pin aperture 56 is disposed at the geometric center of the base member 46. The spline 50 is spaced from the geometric center of the base member 46 in a radial arrangement that terminates at outer periphery of the base member 46.

The wall 76 extends outwardly from the base member 46 in a parallel plane forming an anvil like structure. A top portion 77 of the wall 76 is in a piano-concave form with a distal end portion of the top 77 having a serrated surface 23 that facilitates the clamping of the umbilical cord. An elongated oval shaped window 78 is disposed in the wall 76 in order to allow any shear pin residue, residual blood or umbilical cord tissue to escape from within the knife assembly 4 during the cutting operation. In this regard, the window 78 has a concave form that corresponds to the plano-concave form of the clamping surface wall 77.

Considering the outer clamping component 26 in greater detail with reference to FIG. 2, the outer clamping component 26 is similar in structure to outer clamping component 22. In this regard, the outer clamping component 26 generally includes a circular base member 48 and wall 86 that is integrally connected to an outer segment portion of the base member 48. On the inner face portion of the base member 48 there is disposed a spline, such as the spline 52, the forms part of the locking arrangement 19 as noted before. A pivot pin aperture 58 is disposed at the geometric center of the base member 48. The spline 52 is spaced from the geometric center of the base member 48 in a radial arrangement that terminates at outer periphery of the base member 48.

The wall 86 extends outwardly from the base member 48 in a parallel plane forming an anvil like structure. A top portion 87 of the wall 86 is in a plano-concave form with a distal end portion of the top 87 having a serrated surface 27 that facilitates the clamping of the umbilical cord. An elongated oval shaped window 88 is disposed in the wall 86 in order to allow any shear pin residue, residual blond or umbilical cord tissue to escape from within the knife assembly 4 during the cutting operation. . In this regard, the window 88 has a concave form that corresponds to the plano-concave form of the clamping surface wall 87.

Considering now the locking arrangement 19 in greater detail with reference to FIGS. 1 and 2, the splines 50 and 52 are configured for free rotation relative to one another in one rotational direction only. More particularly, they are interlocked with one another and may only rotate in a clockwise direction. In this regard, when the inner and outer clamping components fully compress and clamp the umbilical cord, the clamping action is fixed since the respective inner and outer clamping components may not be rotated away from each other in a counter-clockwise direction except as otherwise noted relative to utilization of the release button 15 that unlocks the meshing arrangement between the splines 50 and 52 associated with maternal clamp arrangement 40. That is, by actuation of the release button 15, the splines 50 and 52 are sufficiently pushed apart from one another to allow the inner clamping member 24 and the outer clamping member 26 to be pivotally rotated in a counter-clockwise direction to release the clamping force on the mother segment of the umbilical cord for rapid blood harvesting.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

I claim:

1. A medical knife assembly, comprising:
 a neonatal clamping arrangement having a cutting blade pivotally attached thereto;
 a maternal clamping arrangement, said maternal clamping arrangement being releasably secured to said neonatal clamping arrangement by a plurality of shear pins;
 said shear pins being aligned in a parallel plane and perpendicular to said cutting blade to facilitate their shearing to affect separation of said neonatal clamping arrangement from said maternal clamping arrangement;
 said neonatal clamping arrangement includes an inner clamping member and an outer clamping member; and
 said maternal clamping arrangement includes another inner clamping member and another outer clamping member;
 said inner clamping member and said another inner clamping member being temporarily secured together by an individual one of said plurality of shear pins;
 said outer clamping member and said another outer clamping member being temporarily secured together by at least another one of said plurality of shear pins;
 wherein said inner clamping member and said another inner clamping member are pivotally connected to said outer clamping member and said another outer clamping member to effect relative pivotal motion therebetween;

wherein said cutting blade is pivotally mounted and releasaibly secured between said inner clamping member and said another inner clamping member;

wherein said cutting blade includes a base member having a circular spline on an outer face thereof;

said circular spline interlocking with another spline disposed on an adjacent inner clamping member to permit pivotal motion between said cutting blade and said adjacent inner clamping member in one rotational direction only.

2. A medical knife assembly according to claim 1, wherein said adjacent inner clamping member includes another base member having another circular spline on its outer face;

said another circular spline interlocking with yet another spline disposed on an adjacent outer clamping member to permit pivotal motion between said inner clamping member and said adjacent outer clamping member in one rotational direction only.

3. A medical knife assembly according to claim 2, wherein said cutting blade base member includes another circular spline disposed on another outer face thereof;

said another circular spline interlocking with yet another spline disposed on another adjacent inner clamping member to permit pivotal motion between said cutting blade and said another adjacent inner clamping member in one rotational direction only.

4. A medical knife assembly according to claim 3, wherein said another adjacent inner clamping member includes yet another base member having yet another circular spline on its outer face;

said yet another circular spline interlocking with another spline disposed on an yet another adjacent outer clamping member to permit pivotal motion between said another adjacent inner clamping member and said yet another adjacent outer clamping member in one rotational direction only.

5. A medical knife assembly, comprising:

a pair of outer clamping components, each outer clamping component including a circular base member having an outer segment portion with a clamping wall integrally connected thereto and extending therefrom with a sufficient thickness to form an anvil-like structure;

a pair of inner clamping components, each inner clamping component including another circular base member having another outer segment portion and another clamping wall integrally connected thereto and extending therefrom with another sufficient thickness to form another anvil-like structure;

wherein said clamping wall includes a top portion with a plano-concave form and wherein a distal end portion of said top portion has a serrated surface that facilitates the clamping of an umbilical chord;

wherein said wall further includes an elongated shaped window to allow resulting residue from cutting an umbilical chord to escape from within the medical knife assembly;

wherein said window has a concave form that corresponds to the plano-concave form of the clamping wall;

wherein said circular base member has an inner face portion and an outer face portion; and said inner face portion having disposed thereon a spline, said spline being disposed in a radial arrangement commencing spaced from a geometric center of said base member and terminating at about an outer periphery boundary of said base member.

6. A medical knife assembly, according to claim 5, wherein said another clamping wall includes a bottom portion with a plano-concave form and wherein a distal end portion of said bottom portion has another serrated surface that facilitates the clamping of the umbilical chord.

7. A medical knife assembly according to claim 6, wherein said another clamping wall further includes another elongated shaped window to allow resulting residue from cutting the umbilical chord to escape from within the medical knife assembly.

8. A medical knife assembly according to claim 7, wherein said another window has a concave form that correspond to the plano-concave form of the another clamping wall.

* * * * *